(12) United States Patent
Jacobsen et al.

(10) Patent No.: US 7,727,180 B2
(45) Date of Patent: Jun. 1, 2010

(54) METHOD AND APPARATUS FOR PRESETTING DEVICE OPERATING LEVELS WITH DISPLAY

(75) Inventors: Stephen C. Jacobsen, Salt Lake City, UT (US); Shane Olsen, Centerville, UT (US); Tomasz J. Petelenz, Salt Lake City, UT (US)

(73) Assignee: Sterling Investments LC, Salt Lake City, UT (US)

( * ) Notice: Subject to any disclaimer, the term of this patent is extended or adjusted under 35 U.S.C. 154(b) by 292 days.

(21) Appl. No.: 11/804,592

(22) Filed: May 17, 2007

(65) Prior Publication Data

US 2008/0009787 A1    Jan. 10, 2008

Related U.S. Application Data

(60) Provisional application No. 60/801,369, filed on May 17, 2006.

(51) Int. Cl.
*A61M 31/00* (2006.01)
(52) U.S. Cl. .......................................... 604/65; 604/67
(58) Field of Classification Search ............. 604/65–67, 604/131–147, 151–155, 246, 890.1–892.1; 600/431–435
See application file for complete search history.

(56) References Cited

U.S. PATENT DOCUMENTS

| | | | |
|---|---|---|---|
| 5,000,739 A | 3/1991 | Kulisz et al. | |
| 5,531,697 A | 7/1996 | Olsen et al. | |
| 5,745,378 A | 4/1998 | Barker et al. | |
| 5,906,597 A | 5/1999 | McPhee | |
| 6,183,441 B1 | 2/2001 | Kriesel et al. | |
| 6,645,175 B2 | 11/2003 | Kriesel et al. | |
| 6,752,787 B1* | 6/2004 | Causey et al. ............... | 604/131 |
| 2002/0123735 A1* | 9/2002 | Rake et al. .................. | 604/407 |
| 2002/0177809 A1* | 11/2002 | Kriesel et al. ............... | 604/132 |
| 2003/0181888 A1* | 9/2003 | Dextradeur et al. ...... | 604/890.1 |

FOREIGN PATENT DOCUMENTS

| | | |
|---|---|---|
| EP | 0951921 | 10/1999 |
| WO | WO 01/70307 | 9/2001 |

* cited by examiner

*Primary Examiner*—Nicholas D Lucchesi
*Assistant Examiner*—Gerald Landry, II
(74) *Attorney, Agent, or Firm*—Thorpe North & Western LLP

(57) ABSTRACT

Techniques for control of fluid delivery from a fluid reservoir by a medical infusion pump are described. Setting of at least one electronically-controllable pumping parameter is determined by the use of one or more mechanical keys. The mechanical key actuates one or more electronic switches of a mechanical key receptacle coupled to the medical infusion pump. The electronic switches are coupled to the medical infusion pump to control the at least one electronically-controllable pumping parameter. Keys can be differently configured to actuate different switches corresponding to particular settings and can include display indicia showing the particular parameter value set by the key.

22 Claims, 4 Drawing Sheets

| Switch State | Flow Rate | | |
|---|---|---|---|
| | Example 1 | Example 2 | Example 3 |
| 000 | invalid | invalid | invalid |
| 001 | 0.5 | 0.1 | 0.5 |
| 010 | 1.0 | 0.2 | 0.7 |
| 011 | 1.5 | 0.4 | 1.0 |
| 100 | 2.0 | 0.8 | 1.5 |
| 101 | 2.5 | 1.6 | 2.2 |
| 110 | 3.0 | 3.2 | 3.0 |
| 111 | 3.5 | 6.4 | 3.8 |

METHOD AND APPARATUS FOR PRESETTING DEVICE OPERATING LEVELS WITH DISPLAY

This application claims the benefit of U.S. Provisional Patent Application No. 60/801,369 filed on May 17, 2006 and entitled "METHOD AND APPARATUS FOR PRESETTING DEVICE OPERATING LEVELS WITH DISPLAY" which is herein incorporated by reference.

FIELD OF THE INVENTION

The present invention relates to portable infusion pumps. More particularly, the present invention relates to control of fluid delivery to a patient from a fluid reservoir by a non-implantable portable infusion pump.

BACKGROUND OF THE INVENTION AND RELATED ART

Certain medical treatments include dispensing of a medication to a patient over an extended interval of time, known as infusion therapy. For example, insulin, HIV drugs, pain medication, nutrients, antibiotics, and anti-cancer treatments are just a few examples of medications which are sometimes used in infusion therapy. In general, infusion therapy includes the moving of an appropriate amount of medication from a fluid reservoir into the patient in a controlled manner.

A number of different pumps suitable for use in infusion therapy are known. For ambulatory patients, a portable infusion pump results in less disruption to the patient's lifestyle and is therefore often preferred. Portable infusion pumps present several design challenges.

One important aspect of infusion therapy is ensuring that the proper amount of medication is delivered to the patient. It is sometimes necessary to be able to adjust the flow rate provided by the infusion pump, since the flow rate required may depend on the medication and the patient. It is also desirable that the cost of a portable infusion pump is kept low.

Programmable infusion pumps are known, which allow the setting of parameters such as flow rate and the like to be set by way of various controls. Controls (e.g., knobs, buttons, etc.) and indicators (e.g., lights, displays, etc.) provided to enable such programming adds undesirable cost to the infusion pump. Additionally, some controls can be difficult or cumbersome to operate.

Many drugs are infused at only a few defined rates and in a few defined volumes. Hence, one known solution is to provide a family of portable infusion pumps, each of which only operates at a single rate/volume setting. Although the individual devices are easy to use and relatively inexpensive, it is necessary to stock several different units to accommodate different prescriptions, which can be inconvenient.

Fixed settings do not work well with some therapies, such as so-called patient controlled analgesia (PCA). In PCA, typically three pump parameter settings are programmed: base flow rate, bolus amount and bolus lockout time. The base flow rate is a regularly delivered amount of medication. The bolus amount is an addition to the base flow rate which is delivered on demand of the patient. A lockout interval limits how frequently the bolus amount is actually administered.

In PCA it is desirable that programming of the pump can only be performed by the physician or assistant, otherwise a patient access can defeat the lockout interval. Known techniques for limiting access include physical covers which mechanically lock in place to prevent access to the controls, and electronic programming systems which require the pump to be placed on a special programming base for settings to be changed. Both approaches are cumbersome and add cost to the pump.

SUMMARY OF THE INVENTION

The inventors have recognized a need for a system to provide easy programming of a medical infusion pump. The present invention includes a system for control of fluid delivery from a fluid reservoir by a medical infusion pump which helps to overcome problems and deficiencies inherent in the prior art. The system can be used to control one or more electronically-controllable pumping parameters of a medical infusion pump. In one embodiment of the present invention, a medical infusion pump has at least one electronically-controllable pumping parameter. A mechanical key receptacle is coupled to the medical infusion pump and configured to receive a mechanical key. At least one electronic switch is disposed proximate to the mechanical key receptacle in a position so it can be selectably actuated by an inserted mechanical key. The actuation (or non-actuation) of the at least one electronic switch controls settings of the at least one electronically-controllable pumping parameter.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, can be arranged and designed in a wide variety of different configurations. Nonetheless, the invention will be described and explained with additional specificity and detail through the use of the accompanying drawings in which:

DETAILED DESCRIPTION OF EXEMPLARY EMBODIMENTS

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

Figure 1:
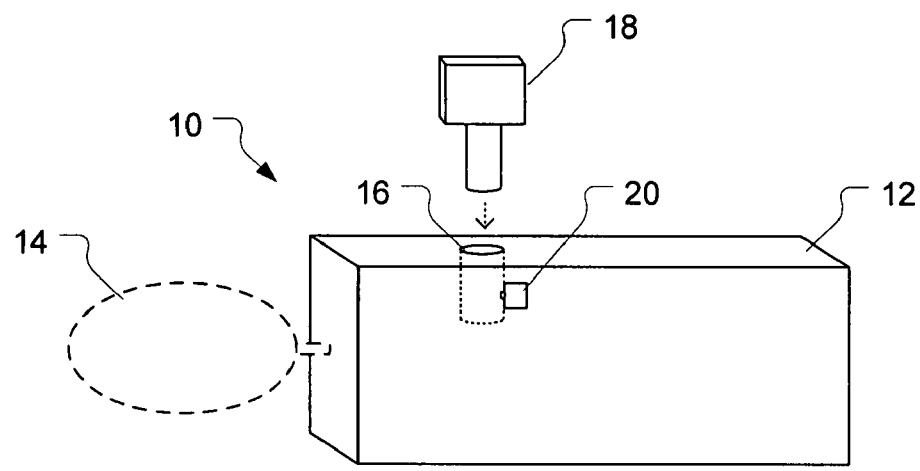
FIG. 1 illustrates a perspective view of a system for control of fluid delivery from a fluid reservoir according to a first exemplary embodiment of the present invention.

With reference to FIG. 1, shown is an illustration of a system for control of fluid delivery from a fluid reservoir according to a first exemplary embodiment of the present invention. Specifically, FIG. 1 illustrates the system 10 as including a medical infusion pump 12 which has at least one electronically-controllable pumping parameter. For example, electronically-controllable pumping parameter can include base flow rate, bolus amount, lockout interval, and the like. The medical infusion pump receives fluid from a fluid reservoir 14 that can be coupled to the pump via various techniques known in the art, including for example a cassette or a tubing line.

A mechanical key receptacle 16 is coupled to the medical infusion pump 12 separately from the fluid reservoir 14. For example, the mechanical key receptacle can include a recess within the housing of the medical infusion pump. The mechanical key receptacle is configured to receive a mechanical key 18. Disposed proximate to the mechanical key receptacle is at least one electronic switch 20, positioned for selectable actuation by the mechanical key. The at least one electronic switch is coupled to the medical infusion pump to control the at least one electronically-controllable pumping parameter. Because the mechanical key arrangement is independent of the fluid reservoir, control of the pumping parameters is independent of the fluid reservoir. Hence, different pumping rates can be selected without requiring replacement of a medication cassette as required for some known infusion pumps. Different mechanical keys can be used to program different values for the at least one electronically-controllable pumping parameter as will be described in further detail below.

Figure 2:
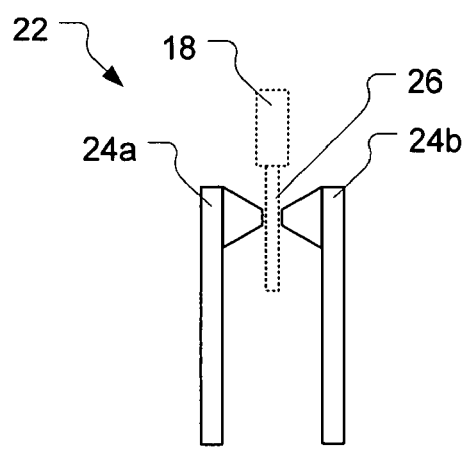
FIG. 2 illustrates a side view of a normally closed-circuit electronic switch, in accordance with an embodiment of the present invention.

Many different arrangements and types of electronic switches can be used within the system 10. For example, FIG. 2 illustrates a normally closed-circuit electronic switch 22, in accordance with an embodiment of the present invention. The normally closed-circuit electronic switch includes a pair of electrical contacts 24a 24b. The electrical contacts are normally in contact with each other to create an open-circuit condition. When a non-conductive key portion 26 is inserted between the contacts, they are deflected to create an open-circuit condition.

Figure 3:
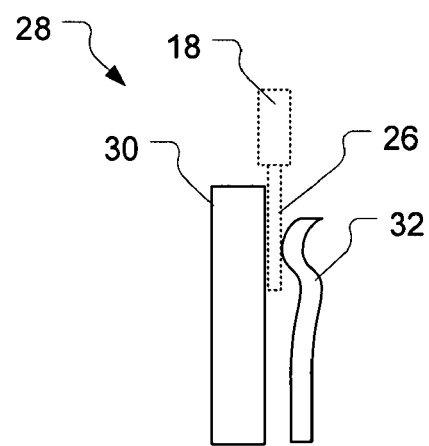
FIG. 3 illustrates a side view of a normally closed-circuit electronic switch in accordance with another embodiment of the present invention.

As another example, FIG. 3 illustrates a normally closed-circuit electronic switch 28 in accordance with another embodiment of the present invention. The normally closed-circuit electronic switch includes a pair of contacts in the form of a base contact 30 and a flexible contact 32 positioned so than inserted non-conductive key portion 26 deflects the flexible contact to create an open-circuit condition.

Figures 4, 5:
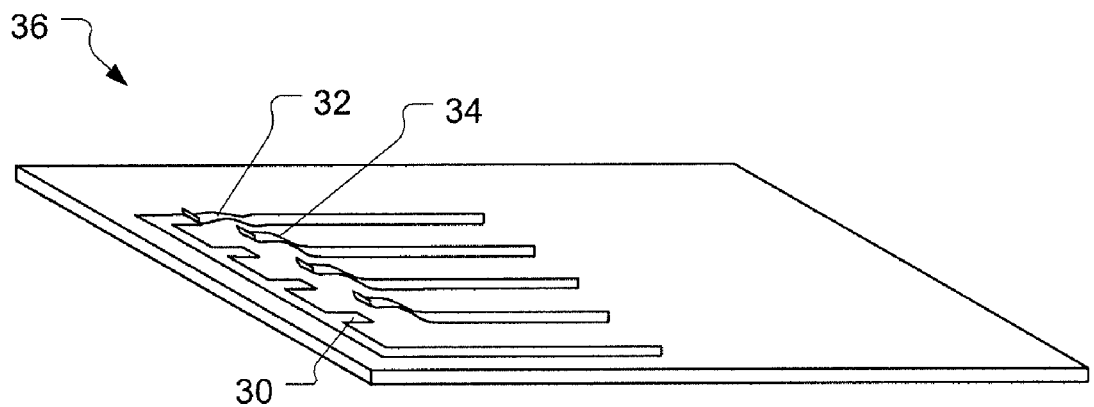
FIG. 4 illustrates a perspective view of a printed circuit board having a plurality of electronic switches in accordance with an embodiment of the present invention.
FIG. 5 illustrates an exemplary encoding of parameter values in accordance with an embodiment of the present invention.

A particularly economical arrangement of an electronic switch 36 can be formed on a printed circuit board as illustrated in FIG. 4 in accordance with an embodiment of the present invention. Printed circuit board traces form one or more base contacts 30, and one or more flexible contacts 32, 34 as illustrated in FIG. 4 in accordance with an embodiment of the present invention. The flexible contacts make contact with the base contact (e.g., as shown for contact 32) to form a closed circuit. When forced upward by a non-conductive key portion (not shown), the circuit is opened (e.g., as shown for contact 34).

Alternately, the electrical contacts can be configured to provide a normally open connection, which is deflected by insertion of a non-conductive key portion to form an open circuit.

The printed circuit board arrangement just described can help to provide for expensive manufacture of an infusion pump, because the switches can be constructed on the same printed circuit board used for other electronics within the pump. For example, a small number of additional parts to implement the flexible contacts of the switches can be inexpensive material, adding little cost. In contrast, dials for setting parameters, user interface panels, programming bases and the like add cost, but in components and required packaging complexity.

How the pumping parameters are controlled through the at least one electronic switch will now be explained in further detail. An electronic switch as just described can encode one bit of digital information. For example, designating a closed-circuit condition as a 1 and an open-circuit condition as a 0, the switch can be actuated to encode either a 1 or 0, depending on whether the switch is closed or open. Accordingly, a plurality of electronic switches can encode a plurality of bits of digital information. For example, two switches can encode two bits of information, providing four different combinations (00, 01, 10, and 11). Three switches can encode three bits of information, providing eight different combinations.

By including multiple switches associated with the mechanical key receptacle, multiple setting values can thus be encoded. For example, the mechanical key can include one or more key portions designed to actuate one or more switches. Each combination of switch actuations can correspond to a particular value. For example, FIG. 5 illustrates values for base flow rate that can be encoded for three switches in accordance with various embodiment of the present invention. The far left column is the pattern encoded by a particular set of open and closed switch conditions. The three columns to the right illustrate three different examples of parameter values corresponding to these switch settings. It will be noted that it is not necessary that the switch pattern correspond to a binary encoding of a desired value; the switch pattern can serve as an index into a table of various values. Many other encodings will occur to one of skill in the art having possession of this disclosure. The case where no switches have been opened corresponds to no mechanical key being inserted into the receptacle, and thus can be designated an un-programmed state. As an option, the operation of the medical infusion pump can be disabled so that no pumping occurs when in this state. As another option, a default parameter value can be set when no mechanical key has been inserted into the receptacle.

Figure 6:
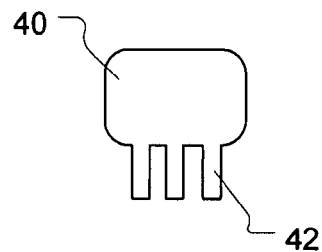
FIG. 6 illustrates a side view of a mechanical key configured for use with the switch arrangement of FIG. 4 in accordance with an embodiment of the present invention.

A mechanical key used with the system can thus include portions which interact with the at least one electronic switch to encode a particular parameter value. For example, FIG. 6 illustrates a mechanical key 40 configured for use with a switch arrangement similar to FIG. 4, in accordance with an embodiment of the present invention. The mechanical key includes tabs 42 positioned to mechanically actuate at least one of the electronic switches. More particularly, the tabs force apart contacts to change at least one of the electronic switches from a closed-circuit to an open-circuit condition. Various arrangements of one, two, or three tabs, can be included to selectively actuate one or more of the three switches to encode the parameter values illustrated in FIG. 5. A set of mechanical keys, each having a different unique arrangement of tabs, can thus encode a number of different parameter values, the particular value encoded by each key determined by the particular unique arrangement of the key tabs.

Figure 7:
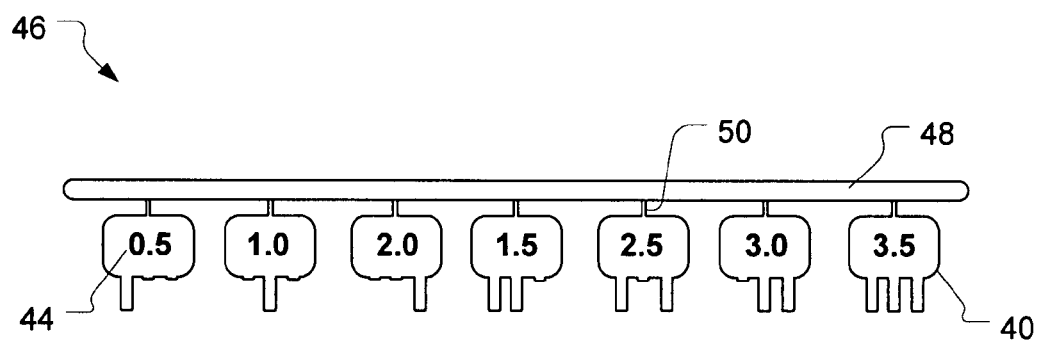
FIG. 7 illustrates a side view of a set of mechanical keys in accordance with an embodiment of the present invention.

For example, as illustrated in FIG. 7, a set 46 of mechanical keys 40, one key for each possible arrangement of tabs (and thus each possible preset value), can be molded from plastic. The keys can be arranged on a holding bar 48, attached by small breakable tabs 50, in an arrangement similar to that used for plastic model parts. Individual keys can be easily detached from the holding bar by twisting the key to break the small breakable tab. Such an arrangement is easily and inexpensively manufactured, for example, by injection molding.

Optionally, the mechanical key 40 can also include a display indicia 44 corresponding to the parameter value encoded by the key. For example, the display indicia can be provided by text or figures, graphics, color, and the like. By including the display indicia, the mechanical key also functions as a display device, allowing a user to easily see what value the pump parameter has been set to. Thus, an electronic display need not be included with the medical infusion pump, helping to reduce cost. As an additional benefit, the display is directly tied to the setting of the parameter, reducing the possibility of erroneous display.

Figure 8:
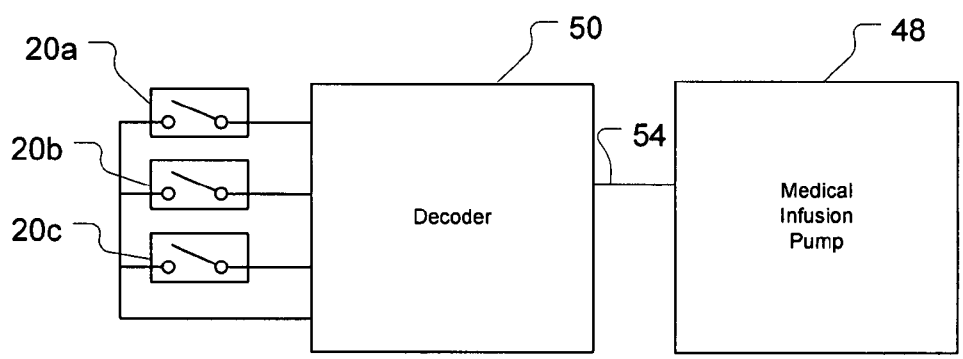
FIG. 8 illustrates an electrical block diagram of the system of FIG. 1 in accordance with an embodiment of the present invention.

FIG. 8 illustrates an electrical circuit block diagram of the system 10 in accordance with an embodiment of the present invention. The electronic switches 20a, 20b, 20c are coupled to a decoder 52. An inserted mechanical key defines a particular arrangement of open-circuit and closed-circuit states for the electronic switches. The decoder converts the pattern of open-circuit and closed-circuit switch states into a particular setting for the parameter value. For example, the decoder can be implemented by digital logic, a memory lookup table, software with a microcontroller, and similar arrangements as will occur to one of skill in the art. The decoder provides appropriate control 54 to the medical infusion pump 12 to cause the medical infusion pump to operate with the desired parameter value setting.

Because the mechanical key can be a simple, passive device, it can be inexpensively manufactured. Keys can thus be easily replaced if lost or discarded. The medical infusion pump can be sold with a complete key set, including extra key sets allowing for the loss or disposal of keys, without adding significant cost.

Programming the medical infusion pump is simplified by the use of the mechanical keys. To program the pump, the key with the desired value is selected and inserted into the pump. Complex menus, displays, and knobs can thus be eliminated, helping to reduce cost. Inserting a mechanical key to program the medical infusion pump is quite simple and relatively foolproof. This can help to reduce the time required for medical professionals to initially set up the medical infusion pump.

Changing the value for which a pump parameter is set is also quite simple, since it involves removing one key and inserting a different key encoded for a different parameter. Using the display indicia on the mechanical key, a medical professional can easily select one of a set of keys to program the desired value.

An additional benefit of the mechanical keys as just described is an inherent level of security. Control systems based on dials, buttons, or electronic menus can easily be changed by a patient unless protected by passwords or physically access limitations. In contrast, by controlling distribution of the mechanical keys (e.g., limiting distribution to doctors or nurses), patients will not be able to easily change settings. This also helps to reduce cost, since complex mechanical or electrical locks can be omitted.

Optionally, the mechanical key receptacle and/or mechanical key can be further configured so that, once inserted, the key cannot be removed. For example, angled barbs can be included in the mechanical key receptacle and arranged so that the key easily slides past the barbs during insertion but engages firmly with the barbs to hinder withdrawal. Various other arrangements to provide one-time key insertion will be known to one of skill in the art.

Figure 9:
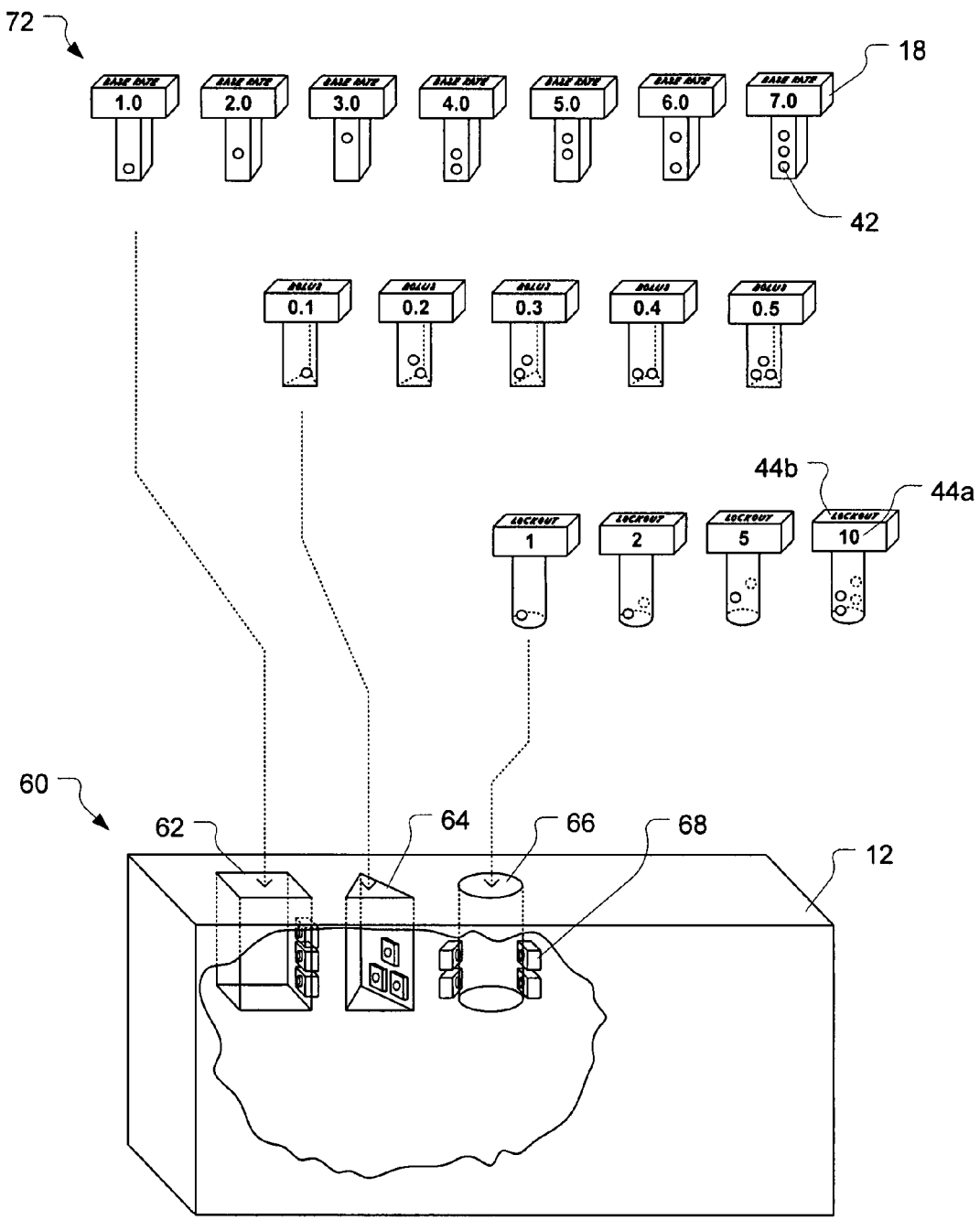
FIG. 9 illustrates a perspective view of a system for control of fluid delivery from a fluid reservoir by a medical infusion pump in accordance with an embodiment of the present invention.

Multiple parameters of a medical infusion pump can also be controlled using similar techniques as will now be explained. FIG. 9 illustrates a system for control of fluid delivery from a fluid reservoir by a medical infusion pump in accordance with an embodiment of the present invention. The system 60 includes a medical infusion pump 12 having a plurality of electronically-controllable pumping parameters. A plurality of mechanical key receptacles 62, 64, 66 is contained within a housing of the medical infusion pump. Each mechanical key receptacle is configured to receive a differently shaped mechanical key, and has at least one electronic switch 68 positioned for selectable actuation by a key tab 42 of an inserted mechanical key. The at least one electronic switch of each receptacle is coupled to the medical infusion pump to control a corresponding electronically-controllable pumping parameter.

For example, a square-shaped receptacle 62 can be configured to control a base flow rate, a triangle-shaped receptacle 64 can be configured to control a bolus amount, and a circular-shaped receptacle 66 can be configured to control a lockout time. To set the parameters of the medical infusion pump 12, a user selects an appropriately-shaped key for the parameter to be set. To program the base flow rate, one of the set 72 of square-shaped keys is selected. Each mechanical key in the set has a square key body shape compatible with insertion into the corresponding square-shaped receptacle. Each of the square-shaped keys has a different arrangement of key tabs 42 to actuate a different selection of electronic switches 68 within the square-shaped receptacle. Accordingly, each key defines a particular parameter to be programmed and a particular value for that parameter. The key is inserted into the receptacle, thereby actuating one or more of the electronic switches. The pattern of actuated switches corresponds to a particular value for the parameter, for example, as discussed above. Electronics within the pump, for example as discussed above, set that parameter to the particular value.

As discussed above, the mechanical keys can include display indicia 44 corresponding to the particular value 44a of the electronically-controllable pumping parameter that is set by the key. The display indicia can also include the particular electronically-controllable pumping parameter 44b that is controlled by the key. For example, each key can be labeled with the parameter that is controlled, and the value to which it is set. Labeling can be provided by color-coding, graphical symbols, text, and the like. As another example, the shape of the key can double as the display indicia.

Summarizing and reiterating to some extent, it can be appreciated from the foregoing that embodiments of the present invention provide an economical system for controlling a medical infusion pump. As taught herein, a set of simple mechanical keys can be inserted into a mechanical key receptacle on a medical infusion pump to program values for the pumping parameters. The mechanical keys include tabs which selectively actuate switches coupled to the medical infusion pump to encode values for the pumping parameters. The mechanical keys and corresponding switches are simple in configuration and thus easily and inexpensively manufactured. Multiple parameters can be controlled using differently shaped keys, and different values can be set for each parameter based on a unique arrangement of the tabs on the key. The mechanical keys can also function as a display, indicating what value the pumping parameter has been set to. Accordingly, expenses associated with knobs, displays, and other user interface features for programming the pump can be avoided.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present: a) "means for" or "step for" is expressly recited in that limitation; b) a corresponding function is expressly recited in that limitation; and c) structure, material or acts that support that function are described within the specification and not in the claim limitation. Accordingly, the scope of the invention should be determined solely by the appended claims and their legal equivalents, rather than by the descriptions and examples given above.

What is claimed is:

1. A system for control of fluid delivery from a fluid reservoir by a medical infusion pump, comprising:
   a medical infusion pump having at least one electronically-controllable pumping parameter;
   a mechanical key receptacle coupled to the medical infusion pump and separate from the fluid reservoir, the mechanical key receptacle being configured to receive a mechanical key having at least one non-conductive key tab; and
   a plurality of electronic switches disposed proximate to the mechanical key receptacle, each switch being selectively actuatable, both individually and in combination with the other switches, by the non-conductive key tab of the inserted mechanical key, the plurality of electronic switches coupled to the medical infusion pump to control the at least one electronically-controllable pumping parameter.

2. The system of claim 1, wherein the at least one electronically-controllable pumping parameter is selected from the group consisting of base rate, bolus, lockout interval, and combinations thereof.

3. The system of claim 1, wherein the plurality of electronic switches comprises at least three normally closed-circuit electrical contacts positioned such that the inserted non-conductive key tab deflects at least one of the electrical contacts to create an open circuit condition.

4. The system of claim 3, wherein the pair of normally closed-circuit electrical contacts comprises a printed circuit board trace.

5. The system of claim 1, wherein the mechanical key comprises
   a key body having a pre-determined shape compatible with the mechanical key receptacle.

6. The system of claim 1, wherein the at least one non-conductive key tab is configured to activate the plurality of electronic switches to encode a binary input corresponding to a particular setting of the at least one electronically-controllable pumping parameter.

7. The system of claim 6, wherein the mechanical key includes a display indicia corresponding to the setting of the at least one electronically-controllable pumping parameter controlled by the key.

8. The system of claim 1, further comprising a decoder coupled to the at least one electronic switch and the medical infusion pump, the decoder being configured to decode a pattern of open and closed states of the at least one electronic switch into a desired setting for the at least one electronically-controllable pumping parameter.

9. The system of claim 1, comprising:
   a plurality of mechanical key receptacles coupled to the medical infusion pump and separate from the fluid reservoir,
   each mechanical key receptacle configured to receive a differently shaped mechanical key,
   each mechanical key receptacle having a plurality of electronic switches, each switch being selectively actuatable, both individually and in combination with the other switches, by an inserted mechanical key and coupled to the medical infusion pump to control a different electronically-controllable pumping parameter.

10. The system of claim 9, comprising a key set separate from the fluid reservoir and comprising a plurality of mechanical keys, each mechanical key
   having a unique key body shape compatible with insertion into a corresponding unique one of the plurality of mechanical key receptacles; and
   having at least one non-conductive key tab positioned on the mechanical key to mechanically actuate at least one of the plurality of electronic switches associated with the mechanical key receptacle when inserted into the compatibly-shaped mechanical key receptacle.

11. The system of claim 10, wherein each mechanical key comprises a display indicia corresponding to the particular electronically-controllable pumping parameter controlled by the key.

12. The system of claim 10, wherein each mechanical key comprises a display indicia corresponding to the particular value of the electronically-controllable pumping parameter controlled by the key.

13. The system of claim 1, wherein the mechanical key receptacle is further configured to hinder withdrawal of a mechanical key once the mechanical key is inserted.

14. A system for control of fluid delivery from a fluid reservoir by a medical infusion pump having at least one electronically-controllable pumping parameter, comprising:
  a mechanical key separate from the fluid reservoir comprising:
  a key body having a shape compatible with insertion into a corresponding mechanical key receptacle associated with the medical infusion pump, and
  at least one non-conductive key tab portion positioned on the key body to mechanically actuate at least one of a plurality of electronic switches disposed proximate to the corresponding mechanical key receptacle when the mechanical key is inserted into the mechanical key receptacle, wherein the plurality of electronic switches control the at least one electronically-controllable pumping parameter.

15. The system of claim 14, wherein the mechanical key comprises a plurality of non-conductive key tab portions positioned on the key body to mechanically actuate the plurality of electronic switches disposed proximate to the corresponding mechanical key receptacle when the mechanical key is inserted into the mechanical key receptacle.

16. The system of claim 15, wherein the plurality of key tab portions corresponds to a switch pattern which encodes one of a plurality of possible values in binary format for the at least one electronically-controllable pumping parameter.

17. The system of claim 15, wherein the plurality of key tab portions corresponds to a switch pattern when encodes a set of particular values in binary format for the at least one electronically-controlled pumping parameter.

18. The system of claim 14, wherein the mechanical key comprises a display indicia corresponding to a value of the at least one electronically-controllable pumping parameter controlled by the mechanical key.

19. A system for control of fluid delivery from a fluid reservoir by a medical infusion pump having at least one electronically-controllable pumping parameter, comprising
  a key set separate from the fluid reservoir and comprising a plurality of mechanical keys, each mechanical key
  having a key body shape compatible with insertion into a compatibly-shaped mechanical key receptacle of the medical infusion pump, and
  having a unique arrangement of at least one non-conductive key tab positioned on the mechanical key to mechanically actuate at least one of a plurality of electronic switches disposed proximate to the compatibly-shaped receptacle when inserted into the compatibly-shaped mechanical key receptacle to encode a binary input setting for controlling the at least one pumping parameter.

20. The system of claim 19, wherein each mechanical key comprises a display indicia corresponding to a pump parameter selected from the group consisting a particular pump parameter value unique to each key, a particular pump parameter controlled by the mechanical key, and a combination of these.

21. The system of claim 19, wherein each key body shape is compatible with insertion into one of a plurality of differently shaped mechanical key receptacles of the medical infusion pump, each mechanical key receptacle associated with a different electronically-controllable pump parameter.

22. The system of claim 19, wherein each electronic switch is selectively actuatable, both individually and in combination with the other switches, by the at least one non-conductive key tab.

* * * * *